United States Patent
Suehira

(10) Patent No.: US 9,144,378 B2
(45) Date of Patent: Sep. 29, 2015

(54) OPTICAL COHERENCE TOMOGRAPHY APPARATUS, OPTICAL COHERENCE TOMOGRAPHY METHOD, OPHTHALMIC APPARATUS, METHOD OF CONTROLLING OPHTHALMIC APPARATUS, AND STORAGE MEDIUM

(75) Inventor: Nobuhito Suehira, Kawasaki (JP)

(73) Assignee: Canon Kabushiki Kaisha, Tokyo (JP)

( * ) Notice: Subject to any disclaimer, the term of this patent is extended or adjusted under 35 U.S.C. 154(b) by 251 days.

(21) Appl. No.: 13/093,890

(22) Filed: Apr. 26, 2011

(65) Prior Publication Data
US 2011/0299035 A1    Dec. 8, 2011

(30) Foreign Application Priority Data
Jun. 4, 2010    (JP) .................................. 2010-129352

(51) Int. Cl.
A61B 3/14    (2006.01)
A61B 3/10    (2006.01)
G01N 21/47   (2006.01)

(52) U.S. Cl.
CPC ............. *A61B 3/102* (2013.01); *G01N 21/4795* (2013.01)

(58) Field of Classification Search
CPC .. A61B 3/00663; A61B 3/102; A61B 3/1015; G01B 9/02091
USPC .......... 351/205, 206, 221; 356/450, 451, 456, 356/477, 479; 382/131; 600/407, 425
See application file for complete search history.

(56) References Cited

U.S. PATENT DOCUMENTS

| | | | |
|---|---|---|---|
| 6,377,349 B1 | 4/2002 | Fercher | |
| 7,466,423 B2 * | 12/2008 | Podoleanu et al. | 356/479 |
| 7,823,782 B2 | 11/2010 | Yatagai et al. | |
| 2001/0033364 A1 * | 10/2001 | Cabib et al. | 351/221 |
| 2009/0079993 A1 * | 3/2009 | Yatagai et al. | 356/497 |
| 2010/0226553 A1 | 9/2010 | Suehira | |
| 2010/0226554 A1 | 9/2010 | Suehira | |
| 2011/0058175 A1 | 3/2011 | Suehira | |
| 2011/0096333 A1 | 4/2011 | Suehira et al. | |
| 2011/0098560 A1 | 4/2011 | Suehira et al. | |

FOREIGN PATENT DOCUMENTS

JP    11-325849 A    11/1999

OTHER PUBLICATIONS

U.S. Appl. No. 13/204,953, filed Aug. 8, 2011, Shimoyama et al.
U.S. Appl. No. 13/282,778, filed Oct. 27, 2011, Matsumoto et al.
U.S. Appl. No. 13/286,481, filed Nov. 1, 2011, Suehira et al.
U.S. Appl. No. 13/287,380, filed Nov. 2, 2011, Suehira et al.

* cited by examiner

*Primary Examiner* — Mahidere Sahle
(74) *Attorney, Agent, or Firm* — Fitzpatrick, Cella, Harper & Scinto

(57) ABSTRACT

An optical coherence tomography apparatus which acquires a tomogram of a target object based on a light intensity detected for each wavelength by combining return light of measurement light from the target object with reference light corresponding to the measurement light, the apparatus comprising: a normalization unit adapted to normalize the light intensity detected for the each wavelength based on a transfer function corresponding to the wavelength resolution; and an image formation unit adapted to form a tomogram of the target object from the light intensities normalized by the normalization unit.

48 Claims, 6 Drawing Sheets

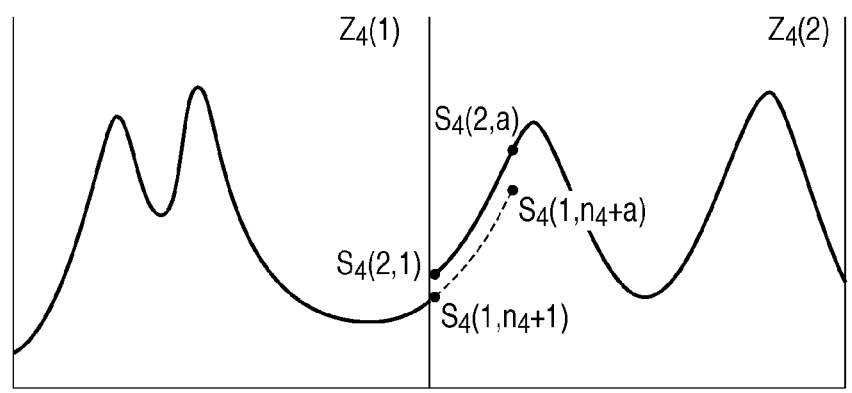
F I G. 6

OPTICAL COHERENCE TOMOGRAPHY APPARATUS, OPTICAL COHERENCE TOMOGRAPHY METHOD, OPHTHALMIC APPARATUS, METHOD OF CONTROLLING OPHTHALMIC APPARATUS, AND STORAGE MEDIUM

BACKGROUND OF THE INVENTION

1. Field of the Invention

The present invention relates to particularly an optical coherence tomography apparatus including an interference optical system which is used in the medical field, an optical coherence tomography method, an ophthalmic apparatus, a method of controlling the ophthalmic apparatus, and a storage medium.

2. Description of the Related Art

Currently, various types of ophthalmic apparatuses using optical devices are used. Such apparatuses include, for example, an anterior ocular segment imaging apparatus, a fundus camera, and a scanning laser ophthalmoscope (SLO). Among them all, an optical coherence tomography (OCT) apparatus (to be referred to as an "OCT apparatus" hereinafter) is an apparatus capable of obtaining a high-resolution tomogram of an object to be examined. This OCT apparatus has been becoming an indispensable apparatus for dedicated retinal outpatient clinics.

For example, the OCT apparatus disclosed in Japanese Patent Laid-Open No. 11-325849 uses low-coherent light as a light source. Light from the light source is split into measurement light and reference light through a splitting optical path such as a beam splitter. Measurement light is light to irradiate an object to be examined such as the eye through a measurement light path. Return light of this light is guided to a detection position through a detection light path. Note that return light is reflected light or scattered light containing information associated with an interface relative to the irradiation direction of light on the object. On the other hand, reference light is light to be guided to the detection position through a reference light path by being reflected by a reference mirror or the like. It is possible to obtain a tomogram of an object to be examined by causing interference between this return light and reference light, collectively acquiring wavelength spectra by using a spectrometer or the like, and performing Fourier transform of the acquired spectra. An OCT apparatus which collectively measures wavelength spectra is generally called a spectral domain OCT apparatus (SD-OCT apparatus).

In an SD-OCT apparatus, a measurement depth $L_{max}$ is represented, as an optical distance $L_{max}$, by a pixel count N of the image sensor of a spectrometer and a spectrum width $\Delta K$ of the frequency detected by the spectrometer according to equation (1). Note that the spectrum width $\Delta K$ is represented by a maximum wavelength $\lambda_{max}$ and a minimum wavelength $\lambda_{min}$. The pixel count N is often an even number, and is generally the factorial of 2, that is 1024 or 2048.

$$L_{max} = \pm \frac{N}{4\Delta K}$$
$$\Delta K = \frac{1}{\lambda_{min}} - \frac{1}{\lambda_{max}}$$
(1)

If, for example, a central wavelength of 840 nm, a band of 50 nm, and a pixel count of 1024 are set, $\lambda_{max}$=840+50/2=840+25=865 nm, $\lambda_{min}$=840−50/2=840−25=815 nm, and N=1024. In this case, optical distance $L_{max}$=3.6 mm. That is, it is possible to perform measurement up to about 3.6 mm on the plus side relative to the coherence gate. The coherence gate is the point at which a reference light path coincides with an optical distance in a measurement light path. When a desired region (a distance in the depth direction) is sufficiently smaller than 3.6 mm (for example, 1 mm or less), the measurement depth can be reduced by decreasing the pixel count of the spectrometer. Decreasing the pixel count is important in order to speed up processing and reduce the data amount. This is because, when measuring a three-dimensional image of the retina, it takes much measurement time and produces a large amount of data. When an object to be examined is a moving object like the eye, in particular, it is required to further shorten the measurement time.

On the other hand, changing the pixel count of a spectrometer is equivalent to changing the resolution of the spectrometer. A problem in this case will be described with reference to FIG. 1. FIG. 1 is a graph obtained by plotting, for each spectrometer resolution, the light intensity measurement results obtained when the position of the coherence gate is moved while a mirror is located at the position of an object to be examined. The ordinate corresponds to the light intensity, and the abscissa to the distance. With an increase in distance from the coherence gate, light intensity attenuation called Roll-Off occurs. The degree of attenuation of a light intensity Int mainly depends on the resolution of a spectrometer and the pixel count of an image sensor. Letting x be a distance variable and a be a coefficient proportional to the resolution of the spectrometer, the degree of attenuation is proportional to a sinc function given by $$\text{Int} \propto \frac{\sin 2\pi x \alpha}{\pi x}$$
(2)

As is obvious from FIG. 1, as a value indicating a resolution increases (from 0.1 nm to 0.2 nm, 0.5 nm, and 1.0 nm), the cycle in which plotted points approach zero is shortened. As described above, images formed from spectrum data from spectrometers having different resolutions differ in light intensity in the depth direction. Differences in light intensity are differences in image contrast. This makes images in the same region look different. That is, with spectrometers having different resolutions, obtained images look different.

In consideration of the above problems, the present invention provides a technique of correcting the contrast differences between images which are caused when wavelength resolutions differ (spectrometers differ in resolution in the case of an SD-OCT) in an FD-OCT apparatus such as an SD-OCT apparatus.

SUMMARY OF THE INVENTION

According to one aspect of the present invention, there is provided an optical coherence tomography apparatus which acquires a tomogram of a target object based on a light intensity detected for each wavelength by combining return light of measurement light from the target object with reference light corresponding to the measurement light, the apparatus comprising: a normalization unit adapted to normalize the light intensity detected for the each wavelength based on a transfer function corresponding to the wavelength resolution; and an image formation unit adapted to form a tomogram of the target object from the light intensities normalized by the normalization unit.

According to one aspect of the present invention, there is provided an ophthalmic apparatus which acquires a tomogram of an eye to be examined based on a light intensity detected for each wavelength by combining return light of measurement light from the eye with reference light corresponding to the measurement light, from a mirror, the apparatus comprising: a normalization unit adapted to normalize the light intensity detected for the each wavelength based on an attenuation function corresponding to a wavelength resolution; and an image formation unit adapted to form a tomogram of the eye from the light intensities normalized by the normalization unit.

According to one aspect of the present invention, there is provided an optical coherence tomography method of acquiring a tomogram of a target object based on a light intensity detected for each wavelength by combining return light of measurement light from the target object with reference light corresponding to the measurement light the method comprising: normalizing the light intensity detected for the each wavelength based on a transfer function corresponding to the wavelength resolution; and forming a tomogram of the target object from the light intensities normalized in normalizing.

According to one aspect of the present invention, there is provided a method of controlling an ophthalmic apparatus which acquires a tomogram of an eye to be examined based on a light intensity detected for each wavelength by combining return light of measurement light from the eye with reference light corresponding to the measurement light, the method comprising: normalizing the light intensity detected for the each wavelength based on an attenuation function corresponding to the wavelength resolution; and forming a tomogram of the eye from the light intensities normalized in normalizing.

Further features of the present invention will be apparent from the following description of exemplary embodiments with reference to the attached drawings.

BRIEF DESCRIPTION OF THE DRAWINGS

FIG. 6 is a view for explaining image adjustment without using any image collectively acquired in the depth direction.

DESCRIPTION OF THE EMBODIMENTS

An exemplary embodiment(s) of the present invention will now be described in detail with reference to the drawings. It should be noted that the relative arrangement of the components, the numerical expressions and numerical values set forth in these embodiments do not limit the scope of the present invention unless it is specifically stated otherwise.

First Embodiment

Figure 2:
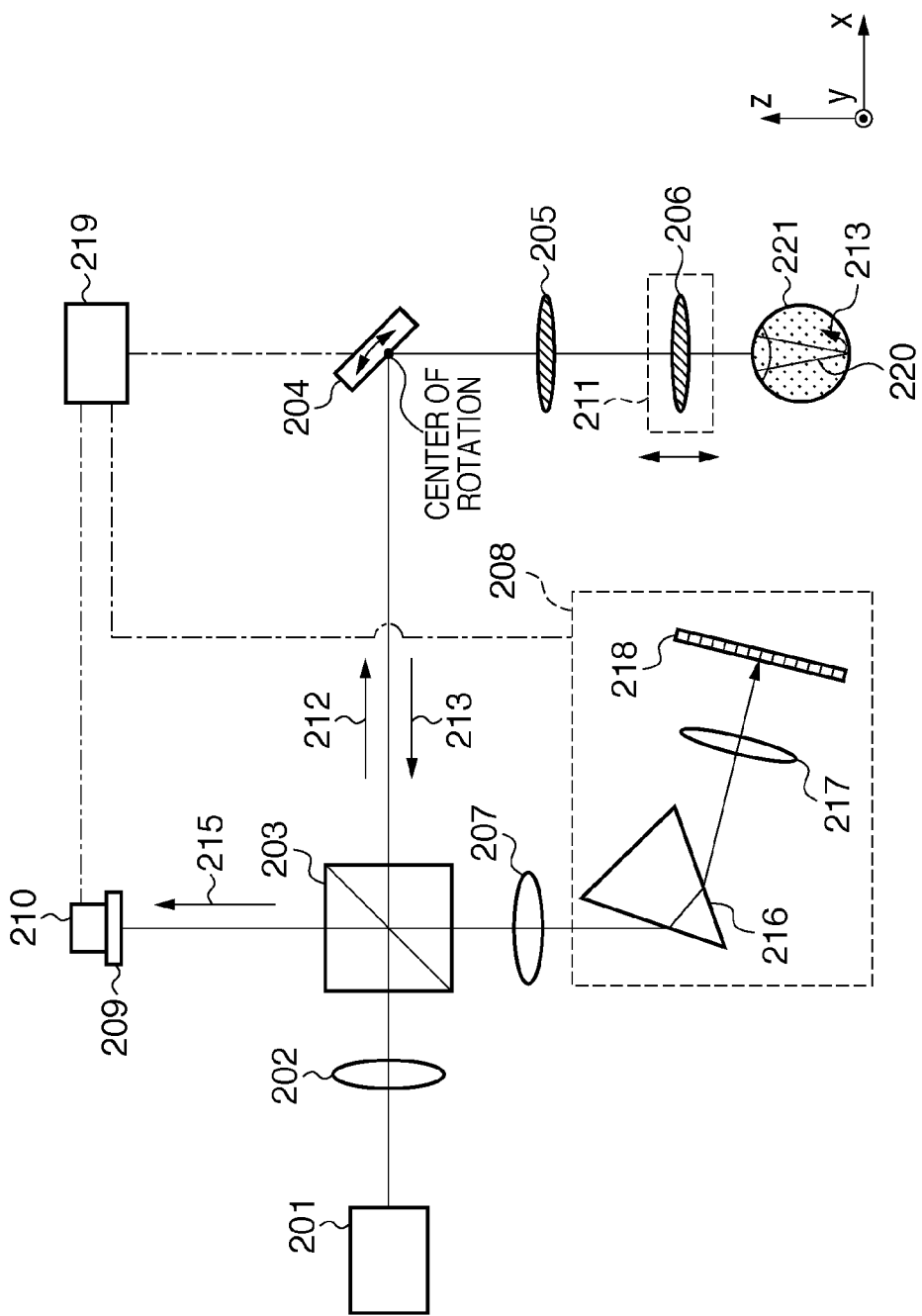
FIG. 2 is a view showing the arrangement of an optical coherence tomography apparatus.

The arrangement of an optical coherence tomography apparatus using an optical coherence tomography method according to the present invention will be described first with reference to FIG. 2.

<Arrangement of Optical System>

The arrangement of an optical coherence tomography apparatus (OCT apparatus) will be described first. The OCT apparatus includes a light source 201, a lens 202, a beam splitter 203, an XY scanner 204, an objective lens 205, a scan lens 206, an imaging lens 207, a spectrometer 208, a reference mirror 209, a mirror driving mechanism 210, a focus driving mechanism 211, and a computer 219. The spectrometer 208 includes a prism 216, a lens 217, and an image sensor 218.

The beam splitter 203 splits the light emitted from the light source 201 into measurement light 212 and reference light 215 through the lens 202. The measurement light 212 reaches an eye 221 (target object) as an object to be examined through the XY scanner 204, the objective lens 205, and the scan lens 206. Return light 213 reflected by a retina 220 of the eye 221 sequentially returns through the scan lens 206, the objective lens 205, the XY scanner 204, and the beam splitter 203. This light reaches the spectrometer 208 through the imaging lens 207. On the other hand, the reference light 215 is reflected by the reference mirror 209. The beam splitter 203 combines the reference light 215 with the return light 213. Note that it is possible to adjust the optical length by causing the mirror driving mechanism 210 to control the reference mirror 209. In addition, the focus driving mechanism 211 allows to control the focus of the measurement light 212.

The light source 201 is an SLD (Super Luminescent Diode) as a typical low-coherent light source. Light from this light source has, for example, a wavelength of 840 nm and a band of 50 nm. Note that the band is an important parameter because it influences the resolution of an obtained tomogram in the optical axis direction. Although an SLD is selected as the light source 201, it is possible to use an ASE (Amplified Spontaneous Emission) source or the like as long as it can emit low-coherent light. Obviously, it is possible to use another kind of light source such as a halogen lamp depending on the type of object to be examined. Note, however, that since a wavelength influences the resolution of an obtained tomogram in the transverse direction, it is good to use a short wavelength, when placing importance on the resolution in the transverse direction.

The spectrometer 208 includes the prism 216, the lens 217, and the image sensor 218 (for example, a line sensor). The spectrometer 208 performs spectroscopy of the measurement light 212 to acquire spectrum data. The image sensor 218 can be a CMOS sensor capable of arbitrarily setting a pixel count N. When decreasing the pixel count N, as the band narrows, the depth resolution of the OCT decreases. For this reason, the band is kept unchanged, and the sampling intervals are increased. Increasing the sampling intervals is equivalent to decreasing the resolution of the spectrometer 208. It is possible to decrease the pixel count N of the image sensor 218 by thinning processing, binning, or the like. It is also possible to change the pixel count N to be imaged by changing the imaging magnification of the lens 217 and changing the spot diameter.

The computer 219 analyzes the wavelength spectrum data captured by the image sensor 218. The computer 219 includes a CPU, a RAM, and a ROM, and has, for example, functions of storing data, displaying images, and issuing a command to perform measurement as well as an analysis function. It is possible to obtain a tomogram of an object to be examined by making the XY scanner 204 raster-scan the measurement light 212 on the object in a direction perpendicular to the optical axis under the control of the computer. Note that an X-Y plane is a plane perpendicular to the optical axis, and Z-axis is an axis parallel to the optical axis. The Z-axis corresponds to an axis in the depth direction of a tomogram.

In this scheme, the mirror driving mechanism 210 modulates the phase of the reference light 215. It is therefore good to allow the mirror driving mechanism 210 to perform control with a precision equal to or higher than 1/100 of a central wavelength. If, for example, the central wavelength is 840 nm, the precision can be about 5 nm. In addition, in order to implement high-speed control, it is possible to combine a coarse motion stage capable of micrometer-order control with a fine motion stage capable of nanometer-order control.

The optical coherence tomography apparatus of the present invention splits light from the light source 201 into the measurement light 212 and the reference light 215 through the splitting optical path. The measurement light 212 irradiates an object to be examined through the measurement light path. In addition, the return light 213 of the measurement light 212 from the object is guided to the detection position through the detection light path. The focus driving mechanism 211 can control the focus of the measurement light 212. On the other hand, the reference light 215 is guided to the detection position through the reference light path. The reference mirror 209 is placed on the reference light path, and it is possible to adjust the coherence gate by controlling the reference mirror 209 using the mirror driving mechanism 210. The light guided to the detection position is decomposed into a wavelength spectrum, which is then analyzed.

Figure 3:
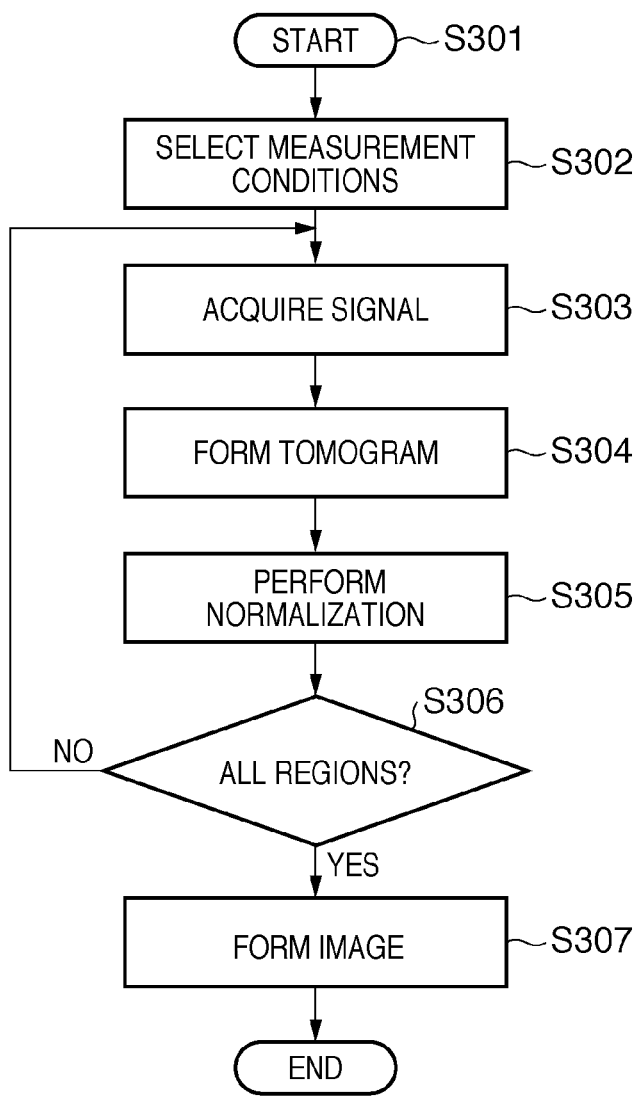
FIG. 3 is a flowchart showing a processing procedure for optical tomography.

A procedure for optical tomography processing according to the present invention will be described with reference to FIG. 3. Note that since this embodiment is applied to an SD-OCT, the resolution of a spectrometer is exemplified. However, the present invention may be applied to wavelength resolution. For example, in the case of an SS-OCT, this is equivalent to the resolution associated with switching of the wavelengths of light from the light source for each given time.

Figure 1:
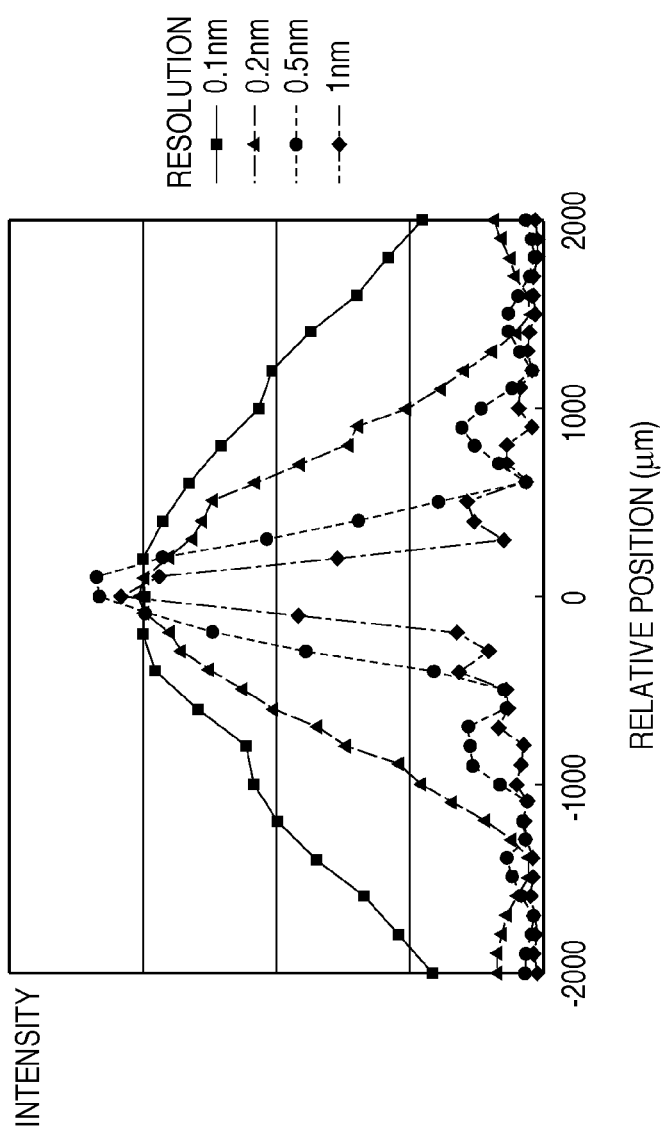
FIG. 1 is a graph obtained by plotting, for each spectrometer resolution, light intensity measurement results obtained when the position of the coherence gate is moved while a mirror is placed at the position of an object to be examined.

In step S301, this apparatus starts measurement processing. In step S302, measurement conditions including the resolution and measurement range of the spectrometer 208 are selected. If, for example, there is a plurality of spectrometers having different resolutions, the apparatus may be configured to be able to select one spectrometer (as the spectrometer 208). In addition, the apparatus may be configured to be able to select one image sensor (as the image sensor 218) from a plurality of image sensors with different pixel counts. Furthermore, the apparatus may be configured to be able to move the lens 217 in the optical axis direction so as to change the range in which an image is formed on the image sensor 218, by changing the position of the lens (using a changing unit (not show) such as a stage mounted on the lens). Assume that in this case, a transfer function corresponding to the resolution of each spectrometer (the pixel count of each image sensor or the position of each lens) is set in advance. This transfer function may be an experimentally obtained attenuation function (a function corresponding to the attenuation of light intensity from the coherence gate in the depth direction), as shown in FIG. 1. An approximate function obtained by approximating FIG. 1 may be used. Note that when the resolution of the spectrometer is fixed, step S302 is not necessary, and it is possible to use a transfer function corresponding to the fixed resolution of the spectrometer. In step S303, a coherence gate and a focus are set at desired positions, and a signal is acquired.

In step S304, this apparatus calculates a tomogram from the signal acquired in step S303. In step S305, the apparatus normalizes a tomogram by using a transfer function corresponding to the resolution of the spectrometer. That is, the apparatus normalizes the light intensity in a measurement region by using this transfer function. For example, normalization is performed by dividing the light intensity in the measurement region by the transfer function.

In step S306, it is determined whether one or two or more measurement regions are all measured. If it is determined that all the measurement regions are measured (YES in step S306), the process advances to step S307. If it is determined that not all the measurement regions are measured (NO in step S306), the process returns to step S303.

In step S307, the apparatus connects the tomograms normalized in step S305 to form an overall image.

In step S308, after the coherence gate and the focus are returned to the initial positions, the measurement processing is terminated.

<Phase Modulation Interference Method>

In this case, a tomographic measurement method based on a phase modulation interference method of detecting the phase difference between the reference light 215 and the measurement light 212 will be described below. First of all, the light intensity from the position (x, y) of an object to be examined is represented by $I(\lambda, \delta)$ using a wavelength $\lambda$ and a phase $\delta$ determined by the position of the coherence gate. Assume that in the case of interference, the light intensity $I(\lambda, \delta)$ from the object is represented by three variables including an incoherent component $I_0$, a coherent component $I_1$, and a phase $\phi(\lambda)$ of the component according to equation (3).

$$I(\lambda,\delta)=I_0(\lambda)+I_1(\lambda)\cos\{\phi(\lambda)+\delta\} \quad (3)$$

In this case, $\delta$ can be changed by moving the position of the coherence gate. For example, $\delta=\pi$ is equivalent to moving the coherence gate by $\lambda_m/4$ when the central wavelength is $\lambda_m$, in consideration of round-trip optical paths.

The 3 frame method changes $\delta$, a total of three times, to 0, $\pi/2$, and $\pi$, and measures light intensity at each time. This makes it possible to obtain three variables, that is, the incoherent component $I_0$, the coherent component $I_1$, and the phase $\phi(\lambda)$ of the component by $$\begin{aligned}\phi(\lambda) &= \tan^{-1}\left\{\frac{-I(\lambda,0)+2I(\lambda,\pi/2)-I(\lambda,\pi)}{I(\lambda,0)-I(\lambda,\pi)}\right\} \\ I_0(\lambda) &= \frac{1}{2}\{I(\lambda,0)+I(\lambda,\pi)\} \\ I_1(\lambda) &= \frac{1}{2}\sqrt{\{-I(\lambda,0)+2I(\lambda,\pi/2)-I(\lambda,\pi)\}^2 + \{I(\lambda,0)-I(\lambda,\pi)\}^2}\end{aligned} \quad (4)$$

The 4 frame method changes $\delta$, a total of four times, from 0 to $3\pi/2$, $\pi/2$ at a time, and measures light intensity at each time. As in the above case, this makes it possible to obtain three variables, that is, the incoherent component $I_0$, the coherent component $I_1$, and the phase $\phi(\lambda)$ of the component by $$\phi(\lambda) = \tan^{-1}\left\{\frac{I(\lambda, \pi/2) - I(\lambda, 3\pi/2)}{I(\lambda, 0) - I(\lambda, \pi)}\right\} \quad (5)$$

$$I_0(\lambda) = \frac{1}{4}\{I(\lambda, 0) + I(\lambda, \pi/2) + I(\lambda, \pi) + I(\lambda, 3\pi/2)\}$$

$$I_1(\lambda) = \frac{1}{2}\sqrt{\{I(\lambda, 0) - I(\lambda, \pi)\}^2 + \{I(\lambda, 3\pi/2) - I(\lambda, \pi/2)\}^2}$$

The 5 frame method changes δ, a total of five times, from 0 to 2π, π/2 at a time, and measures light intensity at each time. As in the above case, this makes it possible to obtain three variables, that is, the incoherent component $I_0$, the coherent component $I_f$, and the phase $\phi(\lambda)$ of the component by $$\phi(\lambda) = \tan^{-1}\left\{\frac{2I(\lambda, \pi/2) - I(\lambda, 3\pi/2)}{I(\lambda, 0) - 2I(\lambda, \pi) + I(\lambda, 2\pi)}\right\} \quad (6)$$

$$I_0(\lambda) = \frac{1}{6}\left\{\begin{array}{l}I(\lambda, 0) + I(\lambda, \pi/2) + 2I(\lambda, \pi) + \\ I(\lambda, 3\pi/2) + I(\lambda, 2\pi)\end{array}\right\}$$

$$I_1(\lambda) = \frac{1}{4}\sqrt{\{2I(\lambda, \pi/2) - 2I(\lambda, 3\pi/2)\}^2 + \{I(\lambda, 0) - 2I(\lambda, \pi) + I(\lambda, 2\pi)\}^2}$$

Transforming the light intensities and phases corresponding to the wavelengths, obtained above, into light intensities and phases corresponding to wave numbers k=1/λ can obtain a tomogram F(z) according to equation (7). Assume that in transformation to wave numbers, resampling and the like are performed at equal intervals relative to the wave numbers in consideration of Fourier transform.

$$F(z) = FT^{-1}\{I_1(k)\exp(j\phi(k))\} \quad (7)$$

where $FT^{-1}$ represents inverse Fourier transform, and j represents an imaginary unit. In general, as the number of frames increases, noise is reduced owing to an averaging effect. On the other hand, as the number of times of measurement increases, the measurement time increases. That is, they have a trade-off relationship. Note that the phase modulation method described above is effective when a coherence gate is placed inside an object to be examined, and a mirror image is generated. That is, when a coherence gate is placed outside the object, since no mirror image is generated, it is possible to obtain the tomogram F(z) by performing Fourier transform of I(λ, δ) as indicated by equation (7). In the second embodiment, a measurement region is divided into a plurality of regions, and a coherence gate is placed at the boundary between the regions. For this reason, a mirror image is generated, and hence the phase modulation method is required. Obviously, the method to be used to remove a mirror image may be a method other than the phase modulation method.

Second Embodiment

Figure 4:
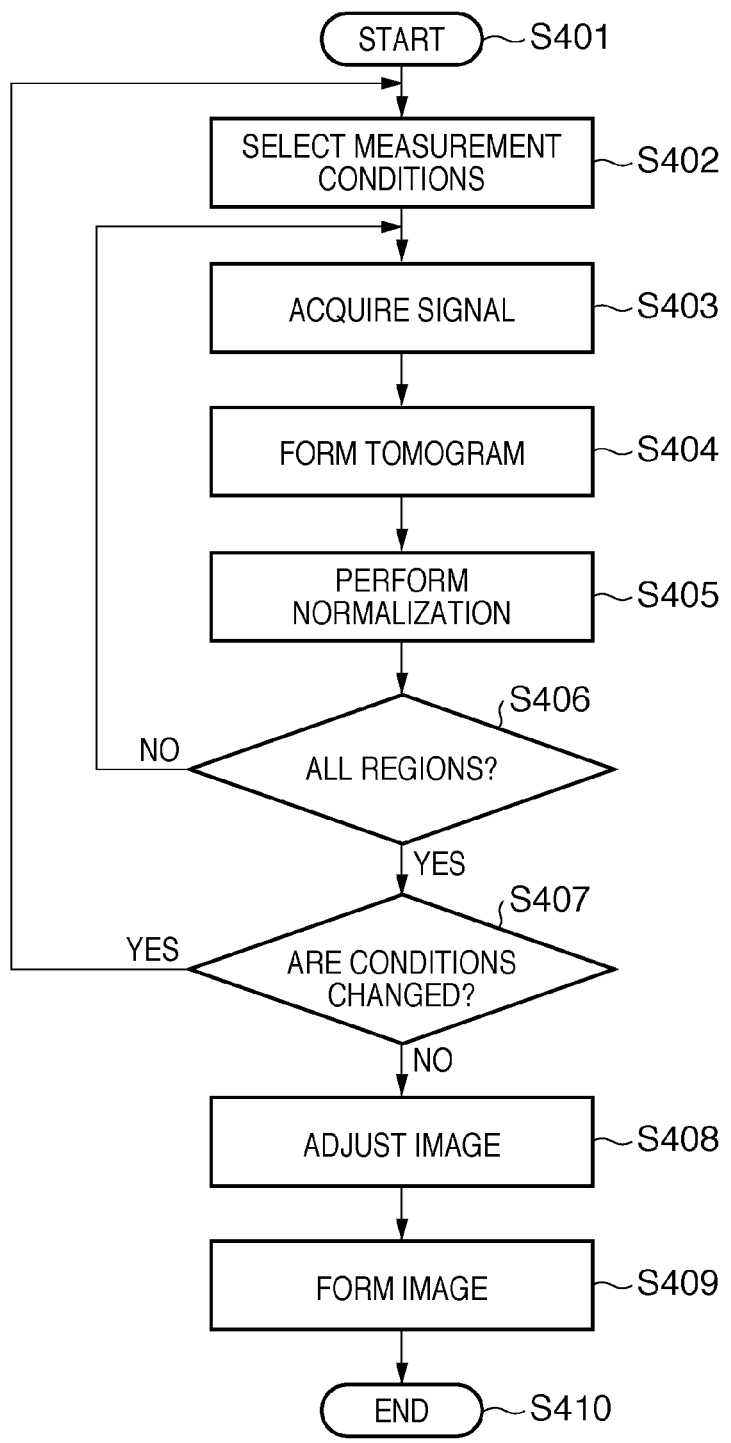
FIG. 4 is a flowchart showing a processing procedure for optical tomography.

<Image Formation>
Measurement to be performed when the transverse resolution is high will be described next with reference to FIG. 4. Note that as the transverse resolution increases, the focal depth decreases. This makes it necessary to divide a measurement region. When a measurement region is divided, the measurement time increases, and it is necessary to perform alignment to correct the motion of the eye. In this case, desired regions are collectively measured, and the measurement result is used for alignment.

Figure 5A:
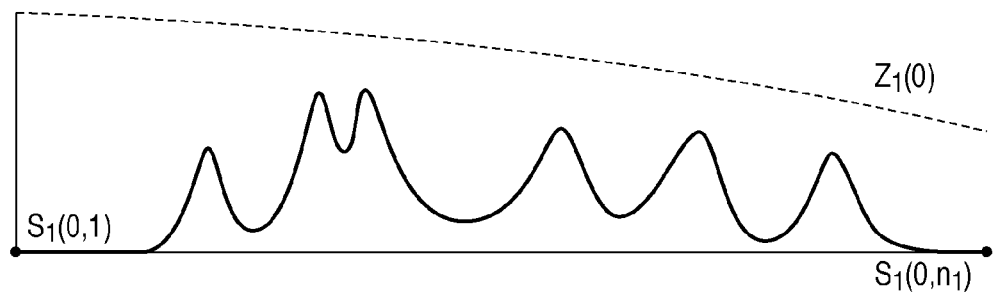
FIG. 5A is a schematic view of light intensity corresponding to one line when information in the depth direction is collectively measured.
Figure 5B:
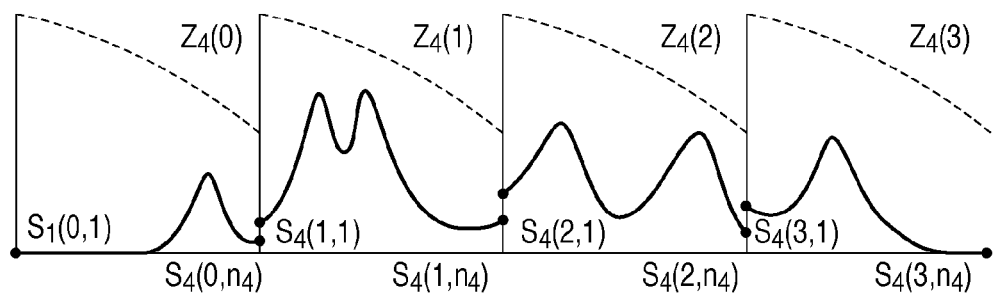
FIG. 5B is a schematic view of light intensity corresponding to one line when information in the depth direction is measured in four parts.
Figure 5C:
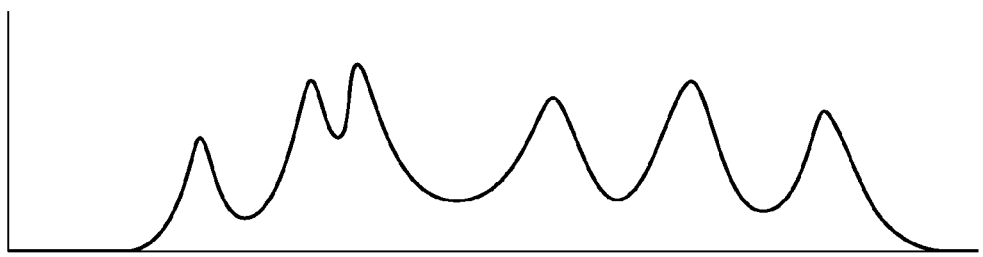
FIG. 5C is a view showing an image formation result.

FIGS. 5A to 5C each are a schematic graph of light intensities corresponding to one line. FIG. 5A shows a case in which information in the depth direction is collectively measured. FIG. 5B shows a case in which information in the depth direction is measured in four parts. FIG. 5C shows an image formation result. Note that each dotted line indicates a transfer function, which shows a range in which the light intensity becomes half.

In step S401, the apparatus starts measurement processing.

In step S402, the operator selects measurement conditions. The measurement conditions include a depth resolution, a transverse resolution, a measurement range, and the resolution of a spectrometer. In addition, when performing measurement upon dividing the measurement range into one or two or more measurement regions, the selection of measurement conditions may include designation of a specific number by which the measurement region is divided. A depth resolution is determined by the band and focal depth of a light source. A transverse resolution is determined by a beam diameter and the like. Since the higher the transverse resolution, the shallower the focal depth, it is necessary to measure the measurement range upon dividing it into several measurement regions. The measurement time is determined by a measurement range, a resolution, the number of frames in the phase modulation interference method, and the like.

In this case, each region is represented by $Z_M(i)$, and the data of a tomogram in each region is represented by $S_M(i, k)$. In this case, M is the number of measurement regions, and i is a measurement region number, which ranges from 0 to M−1. If, therefore, the number of measurement regions is 1, M is 1. If the number of measurement regions is 4, M is 4. In addition, k is an element, which is an integer satisfying 0 to N−1. N is the pixel count of an image sensor.

In step S403, the apparatus acquires a signal. In order to measure the desired measurement region $Z_M(i)$, the apparatus adjusts a coherence gate and a focus. In this case, the apparatus starts measurement from $Z_M(0)$. At the position of the measurement region $Z_M(0)$, since the object to be examined is the eye, the coherence gate is set on the cornea side relative to the retina. Note that the apparatus controls the coherence gate to make the position of $S_M(i−1, n_M)$ of each measurement region $Z_M(i)$ coincide with the position of $S_M(i, 0)$. In addition, the apparatus performs measurement corresponding to the required number of frames, as described in association with the phase modulation interference method, for each measurement region $Z_M(i)$. In this case, $n_m$ can be a value satisfying the origin to ½ of the attenuation function represented by equation (2) as well as being smaller than N/2.

In step S404, the apparatus calculates a tomogram from data corresponding to each frame count. Tomograms in the regions $Z_M(i)$ range from $S_M(i, 1)$ to $S_M(i, n_M)$. Note that the data of $S_m(0, 0)$ represents the position of the coherence gate, but does not originate from a slice. For this reason, the data of $S_M(0, 0)$ may be deleted.

In step S405, the apparatus normalizes the light intensity in each measurement region by using a transfer function predetermined for each measurement condition such as the resolution of the spectrometer. Letting $D_M(i, k)$ be the data of a transfer function used for normalization, data $H_M(i, k)$ after normalization is expressed as equation (8). This normalization processing, that is, normalization using a transfer function predetermined for each spectrometer resolution, makes it possible to correct the contrast differences between images generated when spectrometers have different resolutions.

$$H_M(i,k) = S_M(i,k)/D_M(i,k) \quad (8)$$

A transfer function may be a value theoretically calculated as indicated by equation (2) or a value held in advance upon being experimentally obtained as shown in FIG. 1. Obviously, this value may be a value obtained by fitting equation (2) to an experimentally measured value. Note that a transfer function is prepared in accordance with the resolution or pixel count of the spectrometer 208.

In step S406, it is determined whether processing for all the regions is complete. When acquiring a two-dimensional image, for example, the apparatus acquires 512 tomograms by scanning with an X scanner (Y scanner). When acquiring a three-dimensional image, the apparatus acquires 512×512 tomograms by further scanning 512 lines with the Y scanner (X scanner). When acquiring a three-dimensional image while dividing a measuring region into four regions in the depth direction, the apparatus acquires 512×512×4 tomograms. Note that at least a tomogram corresponding to one line is required for alignment, and there is no need to use all tomograms corresponding to 512×512 lines.

In step S407, it is determined whether there is any change in condition. The measurement conditions are changed when, for example, images in the depth direction are acquired in parts upon collective acquisition of them, or when there are both a place to be measured precisely and a place to be measured coarsely.

In step S408, the apparatus adjusts the image. If there is a collectively acquired tomogram as shown in FIG. 5A, it is possible to compare the tomogram as a reference with the tomograms in the respective regions of $Z_4(0)$ to $Z_4(3)$ in FIG. 5B. For example, it is possible to locate the image at a position where the difference from each region is minimized by the least squares method.

Image adjustment without using any collectively acquired image in the depth direction will be described with reference to FIG. 6. FIG. 6 shows normalized images of $Z_4(1)$ and $Z_4(2)$. Since $n_4$ satisfies N/2, $Z_4(1)$ includes data overlapping $Z_4(2)$. In this case, the overlapping data are $S_4(1, n_4+1)$ to $S_4(1, n_4+a)$ and $S_4(2, 1)$ to $S_4(2, a)$. The apparatus adjusts the image with reference to the data of the overlapping portions so as to minimize the differences from them.

In step S409, the apparatus connects the normalized data in the respective measurement regions to visualize the data.

In step S410, the apparatus returns the coherence gate and the focus to the initial positions and terminates the processing.

In this case, the apparatus performs calculation upon placing the coherence gate at the boundary between measurement regions. If, however, i of $S_M(i, k)$ is a low-order component, an error due to the spectrum of a light source may mix in the data. In such a case, it is possible to measure each measurement region while shifting the coherence gate to the minus side of k.

Although this arrangement is that of an SD-OCT, the arrangement can also be applied to an SS-OCT which sweeps the wavelength of the light source. In this case, the wavelength sampling intervals are changed.

According to the present invention, it is possible to correct the contrast differences between even images obtained by spectrometers having different resolutions. This makes it easy to compare a plurality of images obtained by using spectrometers having different resolutions.

Other Embodiments

Aspects of the present invention can also be realized by a computer of a system or apparatus (or devices such as a CPU or MPU) that reads out and executes a program recorded on a memory device to perform the functions of the above-described embodiment(s), and by a method, the steps of which are performed by a computer of a system or apparatus by, for example, reading out and executing a program recorded on a memory device to perform the functions of the above-described embodiment(s). For this purpose, the program is provided to the computer for example via a network or from a recording medium of various types serving as the memory device (for example, computer-readable storage medium).

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

This application claims the benefit of Japanese Patent Application No. 2010-129352 filed on Jun. 4, 2010, which is hereby incorporated by reference herein in its entirety.

What is claimed is:

1. An optical coherence tomography apparatus which acquires a tomogram of an object based on a light intensity detected for each wavelength by combining return light of measurement light from the object with reference light corresponding to the measurement light, the apparatus comprising:
    a selection unit configured to select a measurement range from a coherence gate in a depth direction of the object;
    a normalization unit configured to normalize the light intensity detected for said each wavelength based on the selected measurement range from a coherence gate; and
    an image formation unit configured to form a tomogram of the object from the normalized light intensities.

2. The apparatus according to claim 1, wherein the selection unit selects, as the measurement range from a coherence gate, at least one measurement area constituting a measurement range of the object in the depth direction,
    wherein said normalization unit normalizes, for each selected at least one measurement area, the light intensity detected for said each wavelength based the selected at least one measurement area, and
    wherein said image formation unit forms a tomogram of the object in the measurement range based on the normalized light intensity for each selected at least one measurement area.

3. The apparatus according to claim 2, wherein said image formation unit forms a tomogram of the object in the measurement range by connecting the tomograms normalized for the respective measurement areas by said normalization unit with reference to light intensities, of light intensities of the tomograms in the measurement areas, which overlap each other.

4. The apparatus according to claim 2, further comprising a holding unit configured to hold the tomograms in the measurement range which are normalized by said normalization unit,
    wherein said image formation unit forms a tomogram of the object in the measurement range by connecting the tomograms normalized for the respective measurement areas by said normalization unit with reference to the light intensity of the tomogram held in said holding unit in advance.

5. The apparatus according to claim 1, wherein the selection unit selects a measurement range in the depth direction as the measurement range from a coherence gate, and
    wherein said normalization unit normalizes a light intensity detected for said each wavelength based on the selected measurement range.

6. The apparatus according to claim 1, further comprising:
a spectrometer configured to detect the combined light upon spectroscopy of the light for each wavelength; and
a changing unit adapted to change a resolution of the spectrometer based on the selected measurement range from a coherence gate.

7. The apparatus according to claim 6, wherein said selection unit further selects one spectrometer of a plurality of spectrometers with different resolutions each otherwise identical to said spectrometer, and
wherein said normalization unit normalizes the light intensity detected for said each wavelength based on the selected resolution of a spectrometer.

8. The apparatus according to claim 6, wherein said spectrometer includes a plurality of image sensors with different pixel counts, and
wherein said selection unit further selects one image sensor from the plurality of image sensors with the different pixel counts.

9. The apparatus according to claim 6, wherein said spectrometer includes:
an image sensor, and
wherein the changing unit changes an imaging range of said image sensor based on the selected measurement range from a coherence gate.

10. The apparatus according to claim 1, wherein said image formation unit forms the tomogram by connecting a plurality of tomograms corresponding to the normalized light intensities of each of a plurality of measurement regions of the object in the depth direction.

11. The apparatus according to claim 1, wherein said selection unit selects, as the measurement range from a coherence gate, an optical distance of a measurement region in the depth direction, and
wherein said normalization unit normalizes a light intensity detected for said each wavelength based on the selected optical distance.

12. The apparatus according to claim 1, wherein the tomogram is obtained by using an SS-OCT which sweeps the wavelength of a light source, and
wherein the apparatus further comprises a changing unit adapted to change the swept wavelength sampling intervals based on the selected measurement range from a coherence gate.

13. The apparatus according to claim 1, further comprising a changing unit configured to change a beam diameter of the measurement light based on the selected measurement range from a coherence gate.

14. The apparatus according to claim 1, further comprising a changing unit configured to change a band of the wavelength of the measurement light based on the selected measurement range from a coherence gate.

15. The apparatus according to claim 1, wherein said selection unit further selects a number of measurement regions in the depth direction,
wherein the apparatus further comprises a determination unit configured to determine an optical distance of the measurement region, and
wherein said normalization unit normalizes a light intensity detected for said each wavelength based on the determined optical distance.

16. The apparatus according to claim 6, wherein said spectrometer includes an image sensor and a lens, and
wherein said changing unit changes an imaging range of said image sensor by moving the lens in an optical axis direction of said spectrometer based on the selected measurement range from a coherence gate.

17. The apparatus according to claim 6, wherein said spectrometer includes an image sensor, and
wherein said changing unit changes the pixel count of the image sensor as the resolution of the spectrometer based on the selected measurement range from a coherence gate.

18. The apparatus according to claim 17, wherein said changing unit changes the pixel count of the image sensor by thinning processing.

19. The apparatus according to claim 17, wherein the image sensor is a CMOS sensor.

20. The apparatus according to claim 1, wherein the normalization unit normalizes the light intensity detected for said each wavelength based on a transfer function corresponding to the selected measurement range from a coherence gate.

21. The apparatus according to claim 1, wherein the normalization unit normalizes the light intensity detected for said each wavelength based on the attenuation function corresponding to the selected measurement range from coherence gate.

22. An ophthalmic apparatus which acquires a tomogram of an eye based on a light intensity detected for each wavelength by combining return light of measurement light from the eye with reference light corresponding to the measurement light, from a mirror, the apparatus comprising:
a selection unit configured to select a measurement range from a coherence gate in a depth direction of the eye;
a normalization unit configured to normalize the light intensity detected for said each wavelength based on the selected measurement range from a coherence gate; and
an image formation unit configured to form a tomogram of the eye based on the normalized light intensities.

23. The apparatus according to claim 22, wherein said image formation unit forms the tomogram by connecting a plurality of tomograms corresponding to the normalized light intensities of each of a plurality of measurement regions of the eye in the depth direction.

24. The apparatus according to claim 22, wherein the normalization unit normalizes the light intensity detected for said each wavelength based on a transfer function corresponding to the selected measurement range from a coherence gate.

25. The apparatus according to claim 24, further comprising an adjustment unit configured to adjust a coherence gate on the cornea side of the eye relative to the retina of the eye,
wherein the transfer function is a function corresponding to attenuation of light intensity from the adjusted coherence gate in the depth direction.

26. The apparatus according to claim 25, wherein said selection unit further selects a number of measurement regions of the object in the depth direction, and
wherein said adjustment unit adjusts the coherence gate based on the selected number of measurement regions, after adjusting the coherence gate on the cornea side of the eye relative to the retina of the eye.

27. The apparatus according to claim 25, wherein said image formation unit forms a tomogram of the retina, and
wherein said adjustment unit returns the coherence gate to the initial position after the tomogram is obtained.

28. The apparatus according to claim 22, wherein the normalization unit normalizes the light intensity detected for said each wavelength based on an attenuation function corresponding to the selected measurement range from a coherence gate.

29. An optical coherence tomography method of acquiring a tomogram of an object based on a light intensity detected for each wavelength by combining return light of measurement light from the object with reference light corresponding to the measurement light, the method comprising the steps of:

selecting a measurement range from a coherence gate in a depth direction of the object;

normalizing the light intensity detected for said each wavelength based on the selected measurement range from a coherence gate; and forming a tomogram of the object based on the normalized light intensities.

30. A computer-readable non-transitory storage medium storing a computer program for causing a computer to execute an optical coherence tomography method defined in claim 29.

31. The method according to claim 29, wherein in said selecting step, a measurement range in the depth direction is selected as the measurement range from a coherence gate, and wherein in said normalizing step, a light intensity detected for said each wavelength is normalized based on the selected measurement range.

32. The method according to claim 29, further comprising the steps of:

detecting the combined light upon spectroscopy of the light for each wavelength by a spectrometer; and changing a resolution of the spectrometer based on the selected measurement range from a coherence gate.

33. The method according to claim 29, wherein the tomogram is formed by connecting a plurality of tomograms corresponding to the normalized light intensities of each of a plurality of measurement regions of the object in the depth direction.

34. The method according to claim 29, wherein an optical distance of a measurement region in the depth direction is selected as the measurement range from a coherence gate, and wherein a light intensity detected for said each wavelength is normalized based on the selected optical distance.

35. The method according to claim 29, wherein the tomogram is obtained by using an SS-OCT which sweeps the wavelength of a light source, and wherein the method further comprises changing the swept wavelength sampling intervals based on the selected measurement range from a coherence gate.

36. The method according to claim 29, further comprising changing a beam diameter of the measurement light based on the selected measurement range from a coherence gate.

37. The method according to claim 29, further comprising changing a band of the wavelength of the measurement light based on the selected measurement range from a coherence gate.

38. The method according to claim 29, wherein a number of measurement regions in the depth direction is selected, wherein the method further comprises determining an optical distance of the measurement region, and wherein a light intensity detected for said each wavelength is normalized based on the determined optical distance.

39. The method according to claim 29, wherein the light intensity detected for said each wavelength is normalized based on a transfer function corresponding to the selected measurement range from a coherence gate.

40. The method according to claim 29, wherein the light intensity detected for said each wavelength is normalized based on an attenuation function corresponding to the selected measurement range from a coherence gate.

41. A method of controlling an ophthalmic apparatus which acquires a tomogram of an eye based on a light intensity detected for each wavelength by combining return light of measurement light from the eye with reference light corresponding to the measurement light, the method comprising the steps of:

selecting a measurement range from a coherence gate in a depth direction of the eye;

normalizing the light intensity detected for said each wavelength based on the selected measurement range from a coherence gate; and forming a tomogram of the eye based on the normalized light intensities.

42. A computer-readable non-transitory storage medium storing a computer program for causing a computer to execute a method of controlling an ophthalmic apparatus defined in claim 41.

43. The method according to claim 41, wherein in said forming step, the tomogram is formed by connecting a plurality of tomograms corresponding to the normalized light intensities of each of a plurality of measurement regions of the eye in the depth direction.

44. The method according to claim 41, wherein the light intensity detected for said each wavelength is normalized based on a transfer function corresponding to the selected measurement range from a coherence gate.

45. The method according to claim 41, wherein the light intensity detected from said each wavelength is normalized based on an attenuation function corresponding to the selected measurement range from a coherence gate.

46. The method according to claim 44, further comprising adjusting a coherence gate on the cornea side of the eye relative to the retina of the eye, wherein the transfer function is a function corresponding to attenuation of light intensity from the adjusted coherence gate in the depth direction.

47. The method according to claim 46, wherein in said selecting step, a number of measurement regions of the eye in the depth direction is further selected, and wherein in said adjusting step, the coherence gate is adjusted based on the selected number, after the coherence gate is adjusted on the cornea side of the eye relative to the retina of the eye.

48. The method according to claim 46, wherein in said forming step, a tomogram of the retina is formed, and wherein in said adjusting step, the coherence gate is returned to the initial position after the tomogram is obtained.

* * * * *